(12) United States Patent
Watanabe et al.

(10) Patent No.: US 8,734,424 B2
(45) Date of Patent: May 27, 2014

(54) CATHETER

(75) Inventors: Nobuyoshi Watanabe, Kasugai (JP); Masatomo Ishikawa, Seto (JP)

(73) Assignee: Asahi Intecc Co., Ltd., Nagoya-shi (JP)

( * ) Notice: Subject to any disclaimer, the term of this patent is extended or adjusted under 35 U.S.C. 154(b) by 28 days.

(21) Appl. No.: 13/546,579

(22) Filed: Jul. 11, 2012

(65) Prior Publication Data
US 2013/0018358 A1    Jan. 17, 2013

(30) Foreign Application Priority Data

Jul. 13, 2011  (JP) .................................. 2011-154444

(51) Int. Cl.
*A61M 25/00*   (2006.01)
(52) U.S. Cl.
USPC ............................. 604/524; 604/523; 604/525
(58) Field of Classification Search
USPC ............... 604/523–529, 102.01–102.03, 103, 604/103.03, 103.09, 164.13
See application file for complete search history.

(56) References Cited

U.S. PATENT DOCUMENTS 5,772,641 A    6/1998  Wilson
6,361,529 B1 *  3/2002  Goodin et al. ................. 604/524

FOREIGN PATENT DOCUMENTS

JP  A-2003-164528  6/2003
WO  WO 01/70323 A1  9/2001

OTHER PUBLICATIONS

Nov. 6, 2012 Search Report issued in European Patent Application No. 12175662.1.

* cited by examiner

*Primary Examiner* — Aarti B Berdichevsky
*Assistant Examiner* — Laura Schell
(74) *Attorney, Agent, or Firm* — Oliff PLC

(57) ABSTRACT

A catheter includes a proximal shaft, a distal shaft including a proximal end portion having an inner cavity into which a distal end portion of the proximal shaft is fitted, and a core wire extending through the inner cavity of the distal shaft. The core wire has a proximal end portion that is joined to a cutout portion formed in the distal end portion of the proximal shaft. Joining means are formed along a joint surface between the proximal end portion of the core wire and the cutout portion. When the joining means are divided into first joining means and second joining means along a longitudinal axis of the catheter, a length of one of the first joining means and the second joining means is larger than a length of the other of the first joining means and the second joining means.

6 Claims, 4 Drawing Sheets

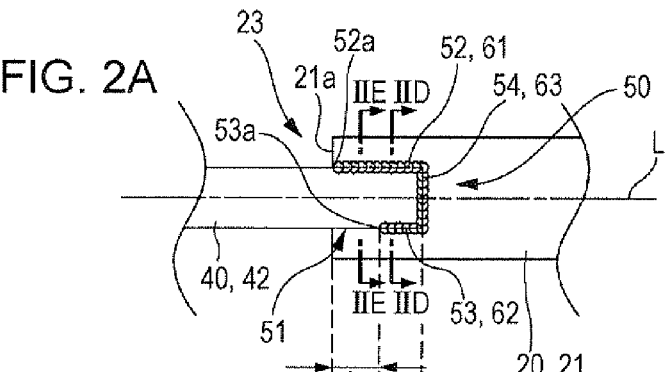
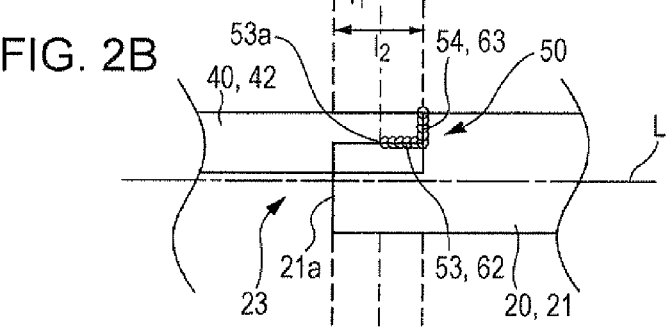
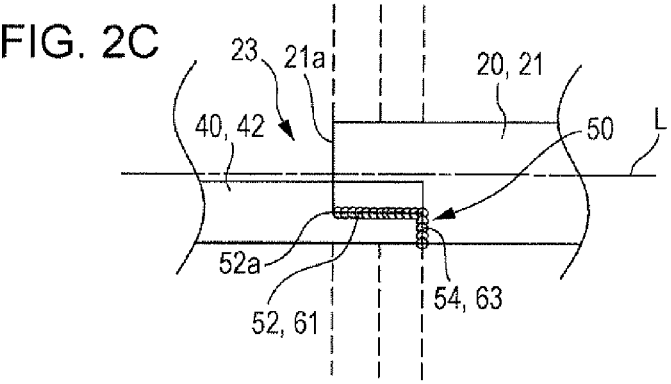
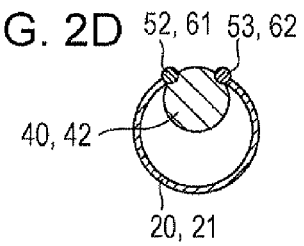
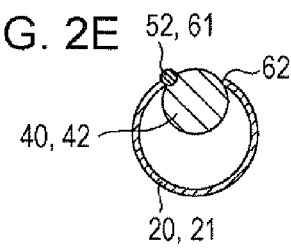

CATHETER

CROSS-REFERENCE TO RELATED APPLICATIONS

This application claims priority to Japanese Patent Application No. 2011-154444 filed in the Japan Patent Office on Jul. 13, 2011, the entire contents of which are incorporated herein by reference.

BACKGROUND

Embodiments of the present invention relate to a medical device. More specifically, embodiments of the present invention relate to a catheter.

A catheter is a medical device that is inserted into a body cavity, such as an abdominal cavity or a lumen, such as a ureter or a blood vessel, to inject a medicine into a lesion or to drain a bodily fluid.

A balloon catheter is a type of catheter used for percutaneous transluminal coronary angioplasty. Guided by a guidewire that has been inserted into a blood vessel, a balloon catheter can reach a stenosed or obstructed lesion and can restore normal blood flow by dilating the lesion with a balloon.

In general, a balloon catheter includes a proximal shaft that is positioned near an operator, a distal shaft that is joined to the proximal shaft and positioned near a lesion, an inflatable and deflatable balloon that is formed in a distal end portion of the distal shaft, and an inner shaft that is disposed in the inner cavity of the distal shaft and extends through the inner cavity of the balloon (see, for example, Japanese Unexamined Patent Application Publication No. 2003-164528).

A space is formed between the distal shaft and the inner shaft, which is disposed in the inner cavity of the distal shaft. The inner cavity of the proximal shaft, the inner cavity of distal shaft, and the inner cavity of the balloon are connected to each other. Therefore, a liquid, such as a contrast medium or a physiological saline, can be supplied to the inner cavity of the balloon through the inner cavities of the proximal shaft and the distal shaft, and thereby the balloon can be inflated and deflated at will.

The inner shaft has another inner cavity that is isolated from the inner cavities of the proximal shaft, the distal shaft, and the balloon. The catheter can be guided to a lesion by inserting a guidewire through the inner cavity of the inner shaft.

Referring to FIGS. 4A to 4C, the structure of a Related Art balloon catheter described in Japanese Unexamined Patent Application Publication No. 2003-164528 will be described below.

FIG. 4A is a partially enlarged plan view of the Related Art balloon catheter, illustrating a joint portion between a core wire and a proximal shaft, FIG. 4B is a partially enlarged side view of the joint portion of FIG. 4A, and FIG. 4C is a partially enlarged side view of the joint portion of FIG. 4B when a bending force is applied to the joint portion. In FIGS. 4A to 4C, the left side is the distal side, and the right side is the proximal side.

As illustrated in FIGS. 4A and 4B, a distal end portion 421 of a proximal shaft 420 is fitted into the inner cavity of a proximal end portion of a distal shaft 430. A core wire 440 extends through the inner cavities of the distal shaft 430 and the distal end portion 421 of the proximal shaft 420. The proximal end of the core wire 440 is joined to the inner surface of the distal end portion 421 of the proximal shaft 420 through joining means 450 such as a weld.

It is described in Japanese Unexamined Patent Application Publication No. 2003-164528 that, in the Related Art balloon catheter 400, the distal end portion 421 of the proximal shaft 420, which is fitted into the inner cavity of the proximal end portion of the distal shaft 430, is inclined toward the distal end, and thereby change in the rigidity of the Related Art balloon catheter at the boundary between the proximal shaft 420 and the distal shaft 430 can be reduced.

SUMMARY

However, the Related Art balloon catheter 400 described in Japanese Unexamined Patent Application Publication No. 2003-164528 has a problem in that, when the balloon catheter is bent and a bending force is applied to the joint portion as illustrated in FIG. 4C, the force is concentrated at a part of the core wire 440 that is in contact with an end 421a of the distal end portion 421 of the proximal shaft 420, and thereby the core wire 440 is likely to become plastically deformed.

To solve the above-referenced problem, a catheter according to an embodiment of the present invention includes a proximal shaft, a distal shaft including a proximal end portion having an inner cavity into which a distal end portion of the proximal shaft is fitted, and a core wire extending through the inner cavity of the distal shaft. The core wire has a proximal end portion that is joined to a cutout portion formed in the distal end portion of the proximal shaft. Joining means is formed along a joint surface between the proximal end portion of the core wire and the cutout portion. When the joining means is divided into first joining means and second joining means along a longitudinal axis of the catheter, a length of one of the first joining means and the second joining means is larger than a length of the other of the first joining means and the second joining means.

In the catheter according to an embodiment of the present invention, the joint surface may include first to third linear portions that are arranged in an angular U-shape in plan view, the first and second linear portions extending parallel to the longitudinal axis so as to face each other, the third linear portion extending perpendicular to the longitudinal axis and connecting the first and second linear portions to each other. Further, the first joining means may join the first linear portion to the core wire, the second joining means may join the second linear portion to the core wire and a length of the first joining means and a length of the second joining means may be different from each other. In the case where a third joining means that joins the third linear portion to the core wire is provided, the third joining means is divided into two portions along the longitudinal axis of the catheter and these portions are respectively incorporated into the first joining means and the second joining means.

In the catheter according to an embodiment of the present invention, an end of the first joining means may reach an end of the distal end portion of the proximal shaft and an end of the second joining means may be separated from the end of the distal end portion of the proximal shaft.

In the catheter according to an embodiment of the present invention, an end of the first joining means and an end of the second joining means may be separated from an end of the distal end portion of the proximal shaft.

BRIEF DESCRIPTION OF THE DRAWINGS

The foregoing and other objects, features, aspects and advantages of the disclosed embodiments will become more apparent from the following detailed description when taken in conjunction with the accompanying drawings, in which:

FIG. 2A is a partially enlarged plan view of the catheter of FIG. 1, illustrating a joint portion between a core wire and a proximal shaft;

FIG. 2B is a partially enlarged side view of the joint portion of FIG. 2A;

FIG. 2C is a partially enlarged side view of the joint portion, seen from a direction opposite to that of FIG. 2B;

FIG. 2D is a sectional view of the catheter of FIG. 1, taken along line IID-IID of FIG. 2A;

FIG. 2E is a sectional view of the catheter of FIG. 1, taken along line IIE-IIE of FIG. 2A;

DETAILED DESCRIPTION OF EMBODIMENTS

Figure 1:
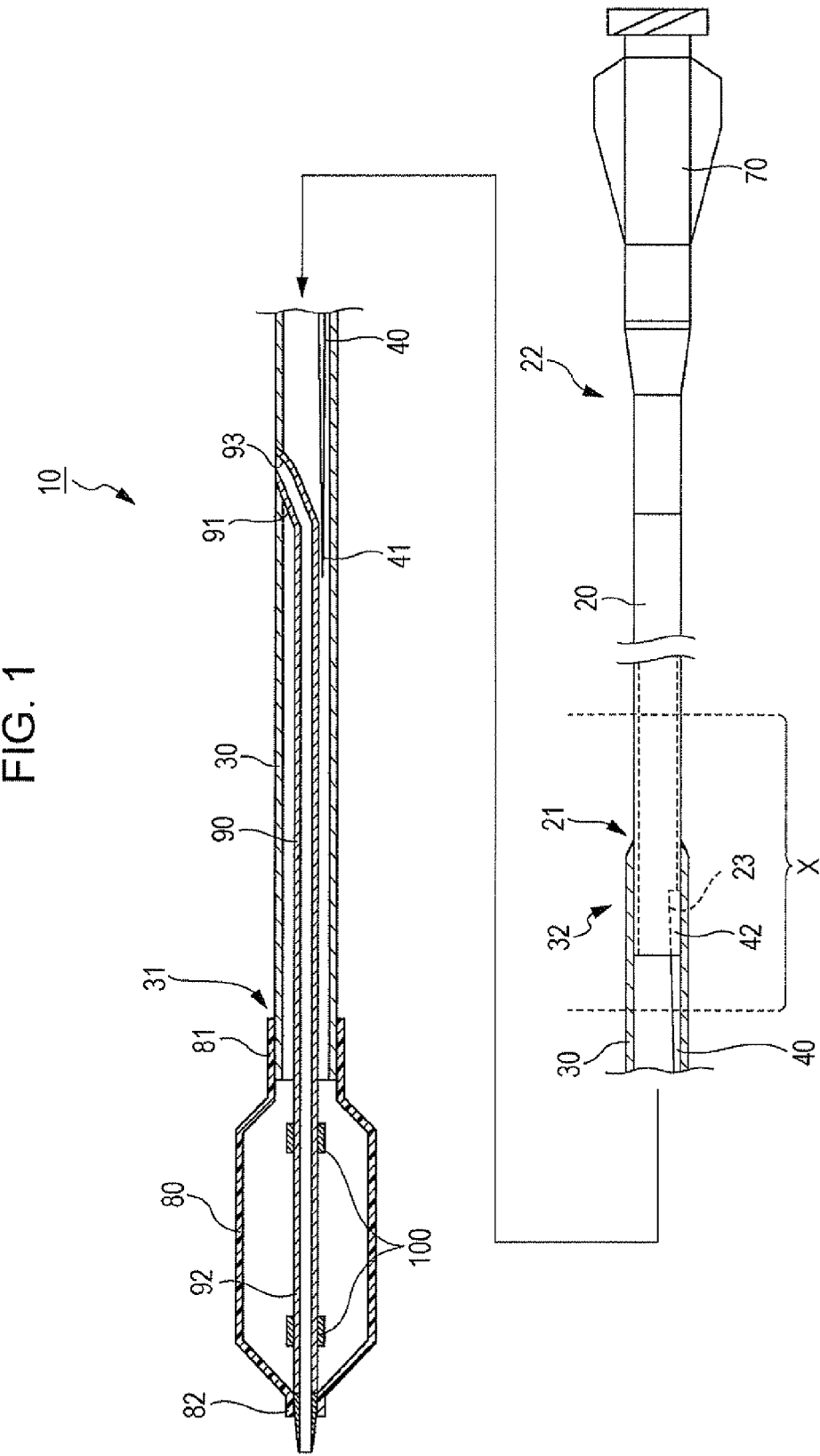
FIG. 1 is an overall schematic view of a catheter according to a first embodiment the present invention.

Referring to FIGS. 1-2E, a catheter according to a first embodiment of the present invention will be described. In particular, referring to FIG. 1, a catheter 10 according to the first embodiment includes a proximal shaft 20, a distal shaft 30, and a core wire 40. A distal end portion 21 of the proximal shaft 20 is fitted into the inner cavity of a proximal end portion 32 of the distal shaft 30. The core wire 40 is disposed in the inner cavity of the distal shaft 30. A proximal end portion 42 of the core wire 40 is joined to a cutout portion 23, which is formed in the distal end portion 21 of the proximal shaft 20.

Referring to FIGS. 2A to 2E, a joint surface 51 with which the cutout portion 23 is joined to the proximal end portion 42 of the core wire 40 includes a first linear portion 61, a second linear portion 62, and a third linear portion 63, which are arranged in an angular U-shape in plan view. The first and second linear portions 61 and 62 extend along a longitudinal axis L of the catheter 10 so as to face each other. The third linear portion 63 extends in a perpendicular direction with respect to the longitudinal axis L and connects the first and second linear portions 61 and 62 to each other.

The first linear portion 61 and the second linear portion 62 have the same length. It is preferable that the length (the entire length $l_2$) of the first linear portion 61 or the length of the second linear portion 62 be in the range of, for example, 1 to 10 mm from the viewpoint of joint strength, and it is more preferable that the length be in the range of 2 to 5 mm. It is preferable that the length of the third linear portion 63 be smaller than that of the first linear portion 61 or the second linear portion 62 from the viewpoint of joint strength, and it is more preferable that the length be in the range of, for example, 0.2 to 1 mm.

Joining means 50, including first and third joining means 52 to 54, are formed along the joint surface 51. To be specific, the first joining means 52 and second joining means 53 respectively join the first linear portion 61 and the second linear portion 62 to the core wire 40. The length of the first joining means 52 is larger than that of the second joining means 53. The third joining means 54 joins the entirety of the third linear portion 63 to the core wire 40. The third joining means 54 need not be formed or only a part of the third linear portion 63 may be joined to the core wire 40.

An end 52a of the first joining means 52 reaches an end 21a of the distal end portion 21 of the proximal shaft 20. An end 53a of the second joining means 53 is separated from the end 21a of the distal end portion 21 of the proximal shaft 20. That is, when the joining means 50 is divided into the first joining means 52 and the second joining means 53 along the longitudinal axis L of the catheter 10, the length of the first joining means 52 is larger than that of the second joining means 53.

Since the length of the first joining means 52 is larger than that of the second joining means 53 in the catheter 10 according to the first embodiment, the joint strength of the joining means 50, which joins the proximal shaft 20 and the core wire 40, differs between parts of the joining means 50 on the right and left sides of the longitudinal axis L of the catheter 10. Therefore, a bending force applied to the joining means 50 when the catheter 10 is bent can be effectively dispersed, so that the core wire 40 is unlikely to be plastically deformed.

In particular, the joint surface 51 includes the first to third linear portions 61 to 63, which are arranged in an angular U-shape. Moreover, the length of the first joining means 52, which joins the first linear portion 61 to the core wire 40, is different from that of the second joining means 53, which joins the second linear portion 62 to the core wire 40. As a result, a bending force applied to the joining means 50 when the catheter 10 is bent can be effectively dispersed along the longitudinal axis L of the catheter 10, so that the core wire 40 is more unlikely to be plastically deformed.

The positions at which a bending force is most likely to be concentrated are presumably in the vicinity of the end 53a of the second joining means 53 and in the vicinity of the end 21a of the distal end portion 21 of the proximal shaft 20. Since the end 53a of the second joining means 53 is separated from the end 21a of the distal end portion 21 of the proximal shaft 20, the positions at which the bending force is most likely to be concentrated are displaced from each other along the longitudinal axis L. As a result, the core wire 40 is more unlikely to be plastically deformed.

It is preferable that the smallest distance between the end 53a of the second joining means 53 and the end 21a of the distal end portion 21 of the proximal shaft 20 be in the range of 1/5 to 4/5 of the entire length $l_2$ of the second linear portion 62. If the smallest distance $l_1$ is in the range of 1/5 to 4/5 of the entire length $l_2$, the amount of displacement between the end 53a of the second joining means 53 and the end 21a of the distal end portion 21 of the proximal shaft 20 is optimized along the longitudinal axis L, so that the core wire 40 is more unlikely to be plastically deformed. On the other hand, if the smallest distance $l_1$ is smaller than 1/5 of the entire length $l_2$, the amount of displacement between the end 53a of the second joining means 53 and the end of the distal end portion 21 of the proximal shaft 20 is too small, so that a bending force may be unlikely to be dispersed. If the smallest distance $l_1$ is larger than 4/5 of the entire length $l_2$, the length of the second joining means 53 is too small, so that the joint strength may be low. In the case where the smallest distance $l_1$ between the end 53a of the second joining means 53 and the end 21a of the distal end portion 21 of the proximal shaft 20 is in the range of 1/5 to 4/5 of the entire length $l_2$ of the second linear portion 62, it is preferable that the smallest distance $l_1$ between the end 53a of the second joining means 53 and the end 21a of the distal end portion 21 of the proximal shaft 20 be in the range of 0.2 to 8 mm, and it is more preferable that the smallest distance $l_1$ be in the range of 0.4 to 3 mm.

The joining means 50 may be, for example, a weld or an adhesive. Between these, it is preferable that the joining means be a weld, and it is even more preferable that that joining means be a weld formed by laser welding using a YAG laser, or the like. In the case where the joining means is a weld, it is more preferable that the joining means be formed such that adjacent portions of the weld overlap each other.

Referring back to FIG. 1, the structure of other parts of the catheter 10 according to the first embodiment will be described below in detail.

The proximal shaft 20 is a tubular member made of a metal such as a stainless steel or a Ni—Ti alloy. A connector 70 is attached to a proximal end portion 22 of the proximal shaft 20.

The distal shaft 30 is a tubular member made of a resin such as a polyamide, a polyamide elastomer, a polyolefin, a polyester, or a polyester elastomer.

An inner shaft 90, which is a tubular member that is made of a resin similar to the material of the distal shaft 30, extends through the inner cavity of the distal shaft 30 with a predetermined space therebetween. A proximal end portion 91 of the inner shaft 90 has an opening 93 formed in an intermediate portion of the distal shaft 30. The inner cavity of the inner shaft 90 is connected to the outside through the opening 93. A distal end portion 92 of the inner shaft 90 protrudes forward from a distal end portion 31 of the distal shaft 30.

A pair of ring-shaped markers 100 are attached to the distal end portion 92 of the inner shaft 90 so as to be separated from each other by a predetermined distance.

A proximal attachment portion 81 of a balloon 80 is fixed to the distal end portion 31 of the distal shaft 30. A distal attachment portion 82 of the balloon 80 is fixed to the distal end portion 92 of the inner shaft 90, which protrudes forward from the distal end portion 31 of the distal shaft 30. Both ends of the balloon 80 are tightly fixed to the shafts, and thereby the balloon 80 is formed at the distal end of the catheter 10.

The material of the balloon 80 may be, for example, a resin such as a low-density polyethylene (LDPE), a high-density polyethylene (HDPE), a linear low density polyethylene (LLDPE), a polyolefin such as an ethylene-vinyl acetate copolymer (EVA), a polyethylene terephthalate (PET), or a polyamide.

The diameter of the core wire 40 decreases from the proximal end portion 42 toward a distal end portion 41 so that the flexibility of the catheter 10 increases toward the distal end. The material of the core wire 40 may be, for example, a stainless steel (SUS), a superelastic alloy such as Ni—Ti alloy, or a piano wire.

In the catheter 10 composed of such members, the inner cavity of the proximal shaft 20, the inner cavity of the distal shaft 30, and the inner cavity of the balloon 80 are connected to each other. When a liquid, such as a contrast medium or a physiological saline, is supplied from an indeflator (not shown), which is attached to the connector 70, to inflate the balloon 80, the liquid passes through the aforementioned inner cavities and inflates or deflates the balloon 80.

A guidewire that has been inserted into a lesion may be passed through the inner cavity of the inner shaft 90, so as to extend to the outside through the opening 93. Thus, the catheter 10 can be inserted into the lesion along the guidewire.

The catheter according to the first embodiment can be made, for example, by using a method including, in addition to the steps of making a known catheter, the steps of forming a cutout portion having the aforementioned shape in a cylindrical proximal shaft by cutting out a part of a distal end portion of the proximal shaft, fitting a proximal end portion of a core wire into the cutout portion, and welding the cutout portion and the proximal end portion to each other such that the length of first joining means is larger than that of second joining means.

A catheter according to a second embodiment has a structure the same as that of the catheter according to the first embodiment except that an end of first joining means and an end of second joining means are both separated from an end of a distal end portion of a proximal shaft. Thus, description of portions of the second embodiment that are the same as those of the first embodiment will be omitted.

Figure 3A:
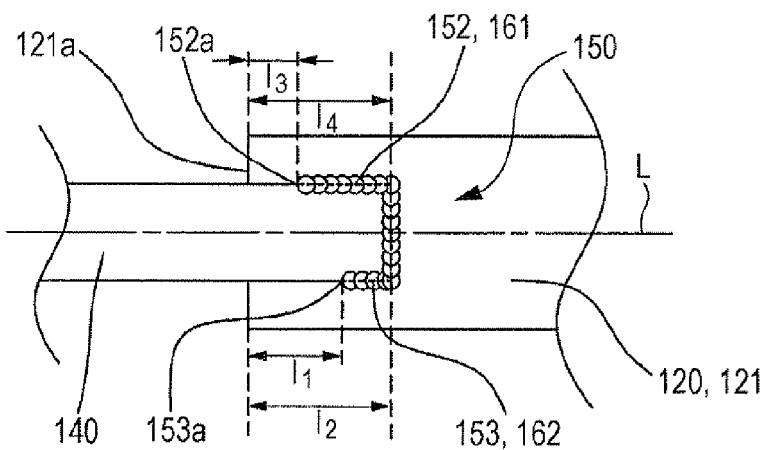
FIG. 3A is partially enlarged plan view of a catheter according to a second embodiment, illustrating a joint portion between a core wire and a proximal shaft.

FIG. 3A is partially enlarged plan view of a catheter according to a second embodiment, illustrating a joint portion between a core wire and a proximal shaft.

Referring to FIG. 3A, an end 152*a* of first joining means 152 is separated from an end 121*a* of a distal end portion 121 of a proximal shaft 120, and an end 153*a* of second joining means 153 is separated from an end 121*a* of a distal end portion 121 of a proximal shaft 120.

Also in the catheter according to the second embodiment, when joining means 150 is divided into the first joining means 152 and the second joining means 153 along the longitudinal axis L of the catheter, the length of the first joining means 152 is larger than that of the second joining means 153. Therefore, the catheter according to the second embodiment has the same advantageous effect as that of the first embodiment.

Moreover, the second embodiment has the following additional effect, which is specific to the second embodiment. In the catheter according to the second embodiment, the end 152*a* of the first joining means 152 is separated from the end 121*a* of the distal end portion 121 of the proximal shaft 120, and the end 153*a* of the second joining means 153 is separated from the end 121*a* of the distal end portion 121 of the proximal shaft 120. The positions at which a bending force is most likely to be concentrated are presumably in the vicinity of the end 152*a* of the first joining means 152, in the vicinity of the end 153*a* of the second joining means 153, and in the vicinity of the end 121*a* of the distal end portion 121 of the proximal shaft 120. Since the end 152*a* of the first joining means 152 and the end 153*a* of the second joining means 153 are separated from the end 121*a* of the distal end portion 121 of the proximal shaft 120, the positions at which a bending force is most likely to be concentrated are displaced from each other along the longitudinal axis L. As a result, a core wire 140 is less likely to be plastically deformed.

It is preferable that the smallest distance $l_1$ between the end 153*a* of the second joining means 153 and the end 121*a* of the distal end portion 121 of the proximal shaft 120 be in the range of ⅖ to ⅘ of the entire length $l_2$ of a second linear portion 162. If the smallest distance $l_1$ is in the range of ⅖ to ⅘ of the entire length $l_2$, the amount of displacement between the end 153*a* of the second joining means 153 and the end 121*a* of the distal end portion 121 of the proximal shaft 120 is optimized along the longitudinal axis L, so that the core wire 140 is more unlikely to be plastically deformed. In this case, it is preferable that the smallest distance $l_3$ be in the range of 0.4 to 8 mm, and it is more preferable that the smallest distance $l_1$ be in the range of 0.6 to 3 mm. On the other hand, if the smallest distance $l_1$ is smaller than ⅖ of the entire length $l_2$, the amount of displacement between the end of the second joining means and the end of the distal end portion of the proximal shaft is too small, so that a bending force may be unlikely to be dispersed. If the smallest distance $l_1$ is larger than ⅘ of the entire length $l_2$, the length of the second joining means is too small, so that the joint strength may be low.

It is preferable that the smallest distance $l_3$, between the end 152a of the first joining means 152 and the end 121a of the distal end portion 121 of the proximal shaft 120, be smaller than the distance $l_1$ and be in the range of 1/5 to 3/5 of the entire length $l_4$ of a first linear portion 161. If the smallest distance $l_3$ is in the range of 1/5 to 3/5 of the entire length $l_4$, the amount of displacement between the end 152a of the first joining means 152 and the end 121a of the distal end portion 121 of the proximal shaft 120 is optimized along the longitudinal axis L, so that the core wire 140 is more unlikely to be plastically deformed. In this case, it is preferable that the smallest distance $l_3$ be in the range of 0.2 to 6 mm, and it is even more preferable that the smallest distance $l_3$ be in the range of 0.4 to 2 mm. On the other hand, if the smallest distance $l_3$ is smaller than 1/5 of the entire length $l_4$, the amount of displacement between the end 152a of the first joining means 152 and the end 121a of the distal end portion 121 of the proximal shaft is too small, so that a bending force may be unlikely to be dispersed. If the smallest distance $l_3$ is larger than 3/5 of the entire length $l_4$, the length of the first joining means is too small, so that the joint strength may be low.

It is preferable that the smallest distance $l_1$ be in the range of 2/5 to 4/5 of the entire length $l_2$ and that the distance $l_3$ be smaller than the smallest distance $l_1$ and be in the range of 1/5 to 3/5 of the entire length $l_4$, because when such conditions are satisfied, the core wire 140 is more unlikely to be plastically deformed. In this case, it is more preferable that the length (the entire length $l_4$) of the first linear portion 161 and the length (the entire length $l_2$) of the second linear portion 162 be in the range of 1 to 10 mm, that the smallest distance $l_1$ be in the range of 0.4 to 8 mm, and that the smallest distance $l_3$ be in the range of 0.2 to 6 mm. It is further preferable that the length (the entire length $l_4$) of the first linear portion 161 and the length (the entire length $l_2$) of the second linear portion 162 be in the range of 2 to 5 mm, that the smallest distance $l_1$ be in the range of 0.8 to 1.5 mm, and that the smallest distance $l_3$ be in the range of 0.4 to 1.0 mm.

The catheter according to the second embodiment can be made by using the method as that of the first embodiment except that the joining means is formed in such a way that an end of the first joining means and an end of second joining means are both separated from an end of the distal end portion of the proximal shaft.

In a catheter according to an embodiment of the present invention, it is sufficient that, when joining means is divided into first joining means and second joining means along the longitudinal axis of the catheter, the length of the first joining means be larger than that of the second joining means. Therefore, catheters according to other embodiments, such as those that are illustrated FIGS. 3B and 3C are also within the technical scope of the present invention.

Figure 3B:
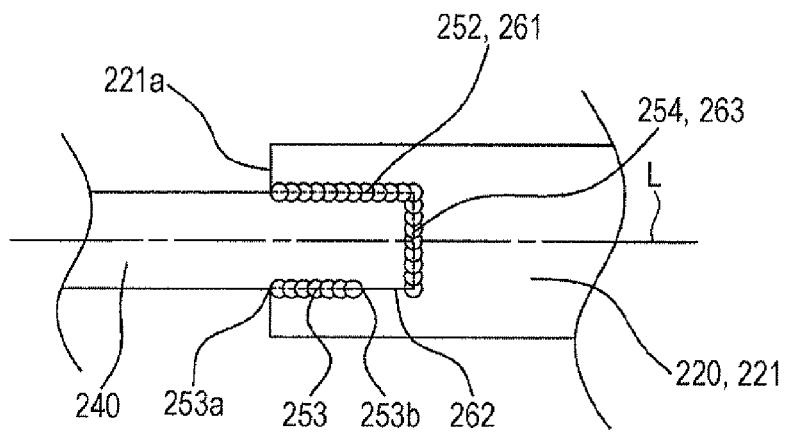
FIGS. 3B and 3C are partially enlarged plan views of catheters according to other embodiments of the present invention, each illustrating a joint portion between a core wire and a proximal shaft.
Figure 3C:
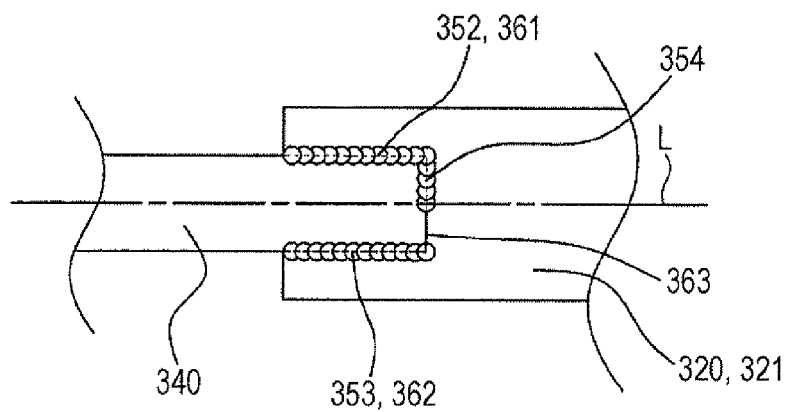
Figure 4A:
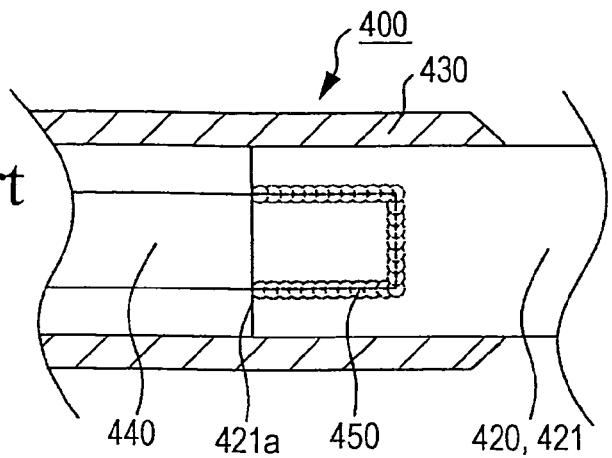
FIG. 4A is a partially enlarged plan view of a Related Art balloon catheter, illustrating a joint portion between a core wire and a proximal shaft.
Figure 4B:
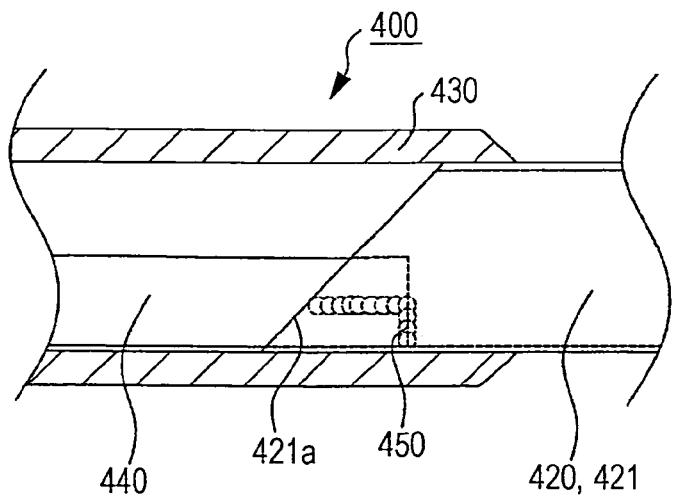
FIG. 4B is a partially enlarged side view of the joint portion of FIG. 4A.
Figure 4C:
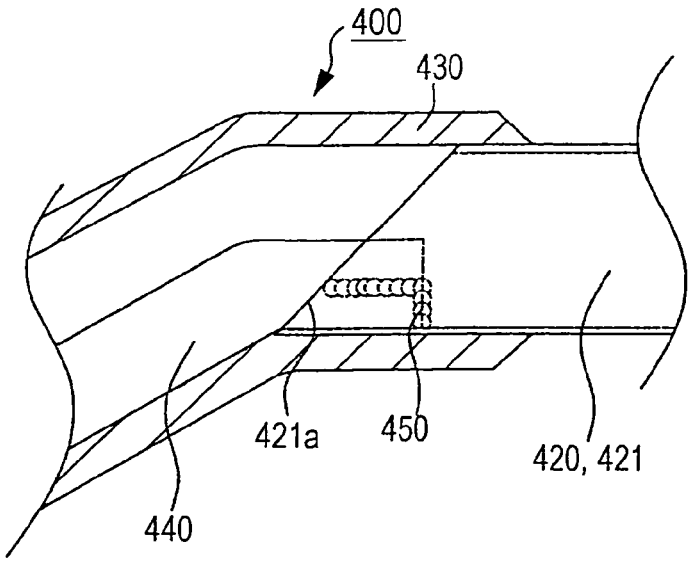
FIG. 4C is a partially enlarged side view of the joint portion of FIG. 4B, when a bending force is applied to the joint portion.

FIGS. 3B and 3C are partially enlarged plan views of catheters according to other embodiments of the present invention, each illustrating a joint portion between a core wire and a proximal shaft.

In the embodiment illustrated in FIG. 3B, first joining means 252 joins the entirety of a first linear portion 261 to a core wire 240, and third joining means 254 joins the entirety of a third linear portion 263 to the core wire 240. On the other hand, second joining means 253 joins part of a second linear portion 262 to the core wire 240. An end 253a of the second joining means 253 reaches an end 221a of a distal end portion 221 of a proximal shaft 220, but an end 253b of the second joining means 253 does not reach the third joining means 254.

In the embodiment illustrated in FIG. 3C, first joining means 352 joins the entirety of a first linear portion 361 to a core wire 340, and second joining means 353 joins the entirety of a second linear portion 362 to the core wire 340. The length of the first joining means 352 is the same as that of the second joining means 353.

On the other hand, third joining means 354 joins only a part of a third linear portion 363 that is positioned between the longitudinal axis L of the catheter and the first joining means 352 to the core wire 340. The third joining means 354 does not join a part of the third linear portion 363 that is positioned between the longitudinal axis L of the catheter and the second joining means 353 to the core wire 340.

In the embodiment illustrated in FIG. 3C, the third joining means 354, which joins only a part of the third linear portion 363 that is positioned between the longitudinal axis L of the catheter and the first joining means 352 to the core wire 340, is incorporated in the first joining means 352. As a result, when the joining means is divided into the first joining means and the second joining means along the longitudinal axis of the catheter, the length of the first joining means is larger than that of the second joining means.

In the embodiments illustrated in FIGS. 3B and 3C, when the joining means is divided into the first joining means and the second joining means along the longitudinal axis of the catheter, the length of the first joining means is larger than the length of the second joining means. As a result, the advantageous effects of the catheter according to embodiments of the present invention can be appropriately obtained.

In a catheter according to embodiments of the present invention, a joint surface between a proximal end portion of a core wire and a cutout portion need not be limited to having an angular U-shape in plan view, as described above. In fact, the joint surface may have an arc shape, or the like. In the case where the joint surface between the proximal end portion of the core wire and the cutout portion has an angular U-shape in plan view, the length of the first linear portion and the length of the second linear portion may be different from each other. In the case where the joint surface between the proximal end portion of the core wire and the cutout portion has an angular U-shape in plan view, the length of the third linear portion may be larger than that of the first linear portion or the second linear portion.

In the embodiments described above, when the joining means is divided into the first joining means and the second joining means along the longitudinal axis of the catheter, the length of the first joining means is larger than that of the second joining means. However, the structure of a catheter according to embodiments of the present invention is not limited to such a structure, and the length of the second joining means may be larger than that of the second joining means.

In the embodiments described above, a rapid exchange balloon catheter is used as an example of a catheter according to the present invention. However, the structure according to the present invention can be appropriately used for an over-the-wire balloon catheter to appropriately obtain the advantageous effects described above. As used herein, the term "over-the-wire balloon catheter" means a catheter in which an inner tube extends to a proximal end portion (proximal portion) of the balloon catheter. The structure according to embodiments of the present invention can be appropriately used for a catheter other than a balloon catheter, such as a penetration catheter for penetrating a stenosed lesion and an injection catheter for injecting a medicine.

A balloon catheter, which is an example of a catheter according to embodiments of the present invention, is usually used for treating a coronary blood vessel. However, a balloon catheter may be used in other manipulations such as a manipulation for dilating a blood vessel in a leg or a dialysis shunt.

While the foregoing embodiments have been shown and described in detail, the foregoing description is in all aspects illustrative and not restrictive. It is therefore understood that numerous modifications and variations can be devised without departing from the spirit and scope of the invention.

What is claimed is:

1. A catheter comprising:
    a proximal shaft having a proximal end portion and a distal end portion, the proximal shaft including a cutout portion formed in the distal end portion;
    a core wire; and
    joining means for joining the core wire to the cutout portion, wherein
    the cutout portion includes,
        a joint portion with which the proximal shaft is joined to the core wire through the joining means,
        a non-joint portion with which the proximal shaft is not joined to the core wire through the joining means, and
    the joint portion is disposed so as to be asymmetrical about a longitudinal axis of the proximal shaft and the core wire.

2. The catheter according to claim 1, wherein
    the cutout portion includes a first linear portion, a second linear portion and a third linear portion, which are arranged in an angular U-shape in plan view, the first linear portion and the second linear portion extending parallel to the longitudinal axis so as to face each other, the third linear portion extending perpendicular to the longitudinal axis and connecting the first linear portion and the second linear portion to each other,
    when the joint portion is divided into a first joint portion and a second joint portion along the longitudinal axis, the first joint portion joins the first linear portion to the core wire and the second joint portion joins the second linear portion to the core wire, and
    a length of the first joint portion is different from a length of the second joint portion.

3. The catheter according to claim 2, wherein
    an end of the first joint portion reaches an end of the distal end portion of the proximal shaft, and
    an end of the second joint portion is separated from the end of the distal end portion of the proximal shaft.

4. The catheter according to claim 2, wherein
    an end of the first joint portion and an end of the second joint portion are both separated from an end of the distal end portion of the proximal shaft.

5. The catheter according to claim 1, wherein
    in the cutout portion, the joint portion is disposed proximally of the non-joint portion.

6. The catheter according to claim 1, wherein
    in a sectional view of the cutout portion, a number of the joining means at a proximal side of the cutout portion is higher than a number of the joining means at a distal side.

* * * * *